(12) United States Patent
Meier

(10) Patent No.: US 7,010,980 B2
(45) Date of Patent: Mar. 14, 2006

(54) METHOD OF DETERMINING THE POROSITY OF A WORKPIECE

(75) Inventor: Rainer Meier, Erlangen (DE)

(73) Assignee: Intelligendt Systems & Services GmbH & Co. KG, Erlangen (DE)

(*) Notice: Subject to any disclaimer, the term of this patent is extended or adjusted under 35 U.S.C. 154(b) by 0 days.

(21) Appl. No.: 10/880,266

(22) Filed: Jun. 28, 2004

(65) Prior Publication Data
US 2004/0261530 A1    Dec. 30, 2004

(30) Foreign Application Priority Data
Jun. 27, 2003   (DE)   ................. 103 29 142

(51) Int. Cl.
*G01N 29/10*   (2006.01)
*G01N 29/20*   (2006.01)
(52) U.S. Cl. .......................... 73/602; 73/627
(58) Field of Classification Search ............... 73/597, 73/598, 599, 600, 602, 620, 627
See application file for complete search history.

(56) References Cited

U.S. PATENT DOCUMENTS

| | | | | |
|---|---|---|---|---|
| 5,303,590 A | * | 4/1994 | Modderman et al. | 73/588 |
| 5,390,544 A | * | 2/1995 | Madras | 73/602 |
| 5,637,799 A | * | 6/1997 | Heyman et al. | 73/600 |
| 2002/0066318 A1 | * | 6/2002 | Dubois et al. | 73/579 |

FOREIGN PATENT DOCUMENTS

| | | | |
|---|---|---|---|
| EP | 538110 A1 | * | 4/1993 |
| SU | 513309 | | 5/1976 |

OTHER PUBLICATIONS

Hans Erik Gundtoft: "Quantitative material characterisation of composites by ultrasonic scanning", $15^{th}$ WCNDT Conference, Rome, Italy, 2000, 6 pg.
L.-K. Shark et al.: "Automatic estimation of ultrasonic attenuation for porosity evaluation in composite materials", $15^{th}$ WCNDT Conference, Rome, Italy, 2000, 7 pgs.
Panametrics, http://www.ndt.net/v07n11.htm., The e-Journal of Nondestructive Testing, Issue vol. 7, No. 11, Nov. 2002, pp. 2.
"NDT.net", http://www.ndt.net/article/az/ut_idxn.htm, pp. 1-5.
"The e-Journal of Nondestructive Testing", http://www.ndt.net/, p. 1.
"Specifications of Digital Ultrasonic Instruments in In-Service Inspection of Nuclear Power Plants", NDTnet, http://www.ndt.net/article/dresd97/csapo/csapo_e.htm, vol. 3, No. 5, May 1998, pp. 1-6.
Krautkrämer, J. et al.: "Werkstoffprüfung mit Ultraschall" [Material Testing with Ultrasound], Springer Verlag, Ed. 5, 1986, pp. 270-275.

(Continued)

Primary Examiner—Hezron Williams
Assistant Examiner—Rose M. Miller
(74) Attorney, Agent, or Firm—Laurence A. Greenberg; Werner H. Stemer; Ralph E. Locher

(57) ABSTRACT

The porosity of a workpiece, in particular a workpiece made of a fiber composite material is determined. An ultrasonic signal is injected into the workpiece and an ultrasonic echo signal is received from the workpiece. The variation of the amplitude of the ultrasonic echo signal with respect to the depth is used as a measure of the porosity of the workpiece material at the respective depth.

6 Claims, 3 Drawing Sheets

OTHER PUBLICATIONS

Hillger, W. et al.: "Ultraschallprüftechnik zur Porositäts-bestimmung in CFK-Bauteilen" [Ultrasound Testing for Porosity Determination in CFK-Components], http://www.ndt.net/article/dgzfp02/papers/p02/p02.htm, 2002, pp. 1-6.

C. Soufflet et al.: "Attenuation Measurement And Flaw Detection In Graphite Epoxy Composites With Random Phase Transducers", *1988 IEEE Ultrasonics Symposium*, Chicago, IL., Oct. 2-5, 1988, pp. 1035-1039, XP 000077086.

V. Deutsch et al.: "Ultraschallprüfung: Grundlagen und Industrielle Anwendungen" [ultrasound checking: basics and industrial applications], chapter 3.4 Fehlernachweis und Gerätejustierung [error detection and device adjustments], 1997, pp. 80-145, XP002301049.

L.-K. Shark et al.: "Automatic estimation of ultrasonic attenuation for porosity evaluation in composite materials", *NDT.NET, Online!* No. 223, 2000, XP002301048.

\* cited by examiner

METHOD OF DETERMINING THE POROSITY OF A WORKPIECE

BACKGROUND OF THE INVENTION

Field of the Invention

The invention relates to a method of determining and assessing the porosity of a workpiece, in particular a workpiece made of a fiber composite material. Workpieces, in particular workpieces made of fiber composite materials, such as for example glass fiber reinforced or carbon fiber reinforced plastics (GFR and CFR respectively), may have a high porosity as a result of the production process that is respectively chosen. This represents a considerable problem in particular in the case of components that are subjected to high mechanical loading and are relevant to safety.

Hans Erik Gundtoft, "Quantitative Material Characterization of Composites by Ultrasonic Scanning", 15th WCNDT Conference Roma 2000, published on the Internet under the address www.ndt.net/article/wcndt00/papers/idn531/idn531.htm, discloses a method of determining the porosity of a fiber composite material in which an ultrasonic signal is injected into the component and either the amplitude of the back-wall echo signal or the attenuation of the transmitted ultrasonic signal is detected and compared with the corresponding signals of a satisfactory component. A lower amplitude of the back-wall echo signal or of the transmitted ultrasonic signal is in this case an indication of the presence of porous locations within the component. This prior art method presupposes that the component has sufficiently parallel surfaces in the region to be assessed to allow usable back-wall echo signals or transmitted ultrasonic signals to be obtained. In addition, it is not possible to ascertain the depth distribution of the pores in the material. However, it may be useful to ascertain the depth distribution of the pores insofar as increased porosity may well be tolerable for example in regions in which the component undergoes only small shearing stresses, whereas it may lead to rapid destruction of the component in zones with higher shearing stresses parallel to the plane of the laminate.

L.-K. Shark and C. Yu, "Automatic Estimation of Ultrasonic Attenuation for Porosity Evaluation in Composite Material", 15th WCNDT Conference Roma 2000, discloses correcting the back-wall echo signal with a so-called wavelet analysis. The ratio between the amplitude of the entry echo signal and the amplitude of the corrected back-wall echo signal are thereby used to assess the porosity.

SUMMARY OF THE INVENTION

It is accordingly an object of the invention to provide a method of determining the porosity of a workpiece which overcomes the above-mentioned disadvantages of the heretofore-known devices and methods of this general type and which makes it possible to ascertain the extent of the porosity and the position in terms of depth.

With the foregoing and other objects in view there is provided, in accordance with the invention, a method of determining the porosity of a workpiece, in particular a workpiece made of a fiber composite material. The novel method comprises:

injecting an ultrasonic signal into the workpiece;

receiving an ultrasonic echo signal from the workpiece; and determining a variation of an amplitude of the ultrasonic echo signal with respect to a depth, and using the variation of the amplitude as a measure of the porosity at the respective depth.

In other words, an ultrasonic signal is injected into the workpiece and an ultrasonic echo signal is received from the workpiece. The variation of the amplitude of the ultrasonic echo signal with respect to the depth in the workpiece is used as a measure of the porosity at the respective depth. Since the dependence of the ultrasonic echo signal on the depth (transit time) is analyzed for the evaluation, it is possible on the basis of this variation also to ascertain findings about the degree of porosity existing at the respective depth.

The invention is based here on the realization that the extent of the ultrasonic signals scattered in the component at a given depth and detected by an ultrasonic receiver as ultrasonic echo signals depends greatly on the degree of porosity and the distribution of the pores in the workpiece. By comparison with a reference workpiece that is free from pores or has few pores or with reference zones on the same workpiece that have few pores, a qualitative assessment can be made concerning the degree of porosity and the porosity distribution within the workpiece. The average slope of the ultrasonic echo signal dependent on the depth has been found here to be a particularly suitable criterion for the assessment of the porosity.

In accordance with an added feature of the invention, the method further comprises:

dividing the workpiece in an area region to be investigated into a plurality of layers of muttually different depths;

placing an ultrasonic test head onto the area region in a test position, injecting the ultrasonic signal into the workpiece with the test head, receiving the ultrasonic echo signal from the workpiece, and measuring the amplitude belonging to each layer; and using a variation of the amplitude with respect to the depth of the layer as a measure of the porosity in the respective layer.

In accordance with an additional feature of the invention, the area region is defined with a number of test positions and the method further comprises averaging the amplitude of the ultrasonic echo signal belonging to the individual layers respectively measured in the individual test positions.

In accordance with another feature of the invention, the amplitudes of the ultrasonic echo signals belonging to a layer are determined by an ALOK (amplitude time locus curves) method.

In accordance with a concomitant feature of the invention, an average slope of the ultrasonic echo signal, in dependence on a depth d, is used as the measure of the porosity.

Other features which are considered as characteristic for the invention are set forth in the appended claims.

Although the invention is illustrated and described herein as embodied in a method of determining the porosity of a workpiece, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
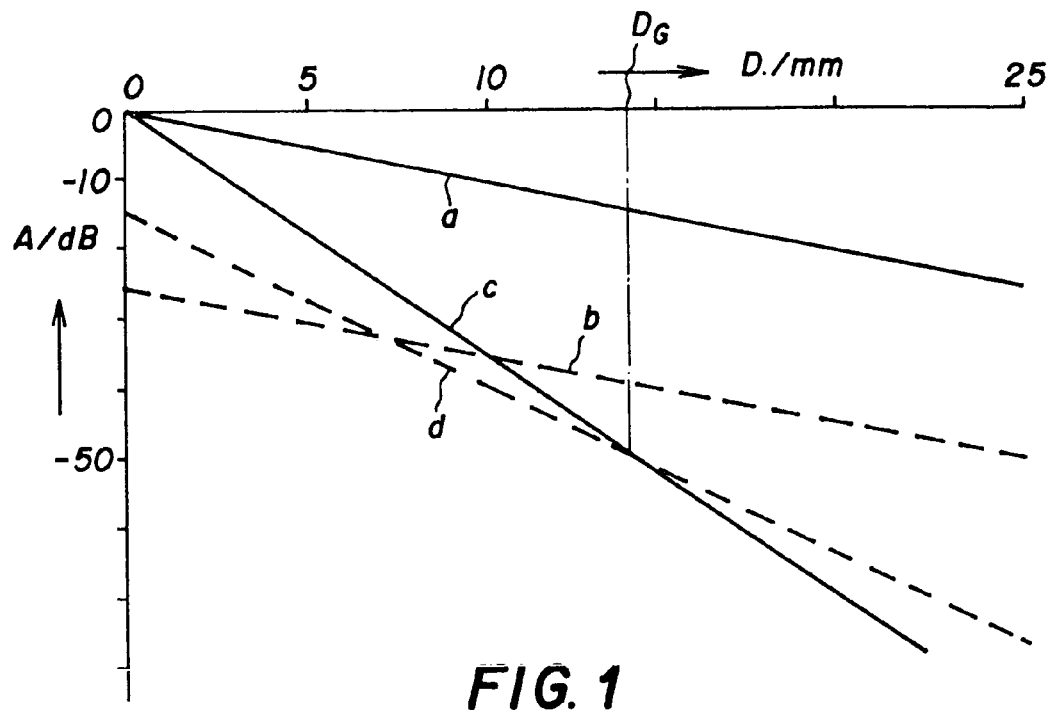
FIG. 1 is a diagram in which the basic variation of the amplitude of the back-scattered ultrasonic echo signal and of the back-wall echo signal in the case of a porous component and a nonporous component is plotted against the thickness of the component.

Referring now to the figures of the drawing in detail and first, particularly, to FIG. 1 thereof, there is shown a diagram plotting the amplitude A of the received ultrasonic echo signal in dependence on the thickness D of the component. Curves a and b respectively show the variation of the amplitude of the back-wall echo signal and backscattered echo signal of a nonporous component, curves c and d respectively show the variation of the amplitude A of the back-wall echo signal and backscattered echo signal of a porous component. The curves a and c then reveal that the amplitude A of the back-wall echo signal decreases to a significantly stronger extent with increasing thickness D of the component in the case of a porous component than in the case of a component with low porosity. According to curve a, an attenuation of the back-wall echo signal by approximately 15 dB is obtained for example for a nonporous component with a thickness D=15 mm. By contrast, the back-wall echo signal in the case of a component of the same thickness d but great porosity is attenuated by almost a further 40 dB. Curves b and d then reveal that the amplitude A of the backscattered echo signals decreases with increasing depth in the component much less in the case of a component with low porosity than in the case of a porous component. Because of the pores that are present, the amplitude A of the backscattered echo signal in the case of a porous component is higher for small depths (in the example to a depth of approximately 7.5 mm) than in the case of a component with lower porosity, but then decreases much more quickly with increasing depth, since on the one hand the ultrasonic signal penetrating to greater depths and on the other hand the backscattered echo signal scattered back from these depths are attenuated on the outward path and return path by scattering at the pores lying above these depths.

In the example, in the case of a limiting thickness or depth $D_G$ of approximately 14 mm, the amplitude A of the back-wall echo signal of a porous component is approximately equal to the amplitude A of the backscattered echo signal, so that the back-wall echo signal can no longer be detected in the case of materials with a greater thickness D.

Figure 2:
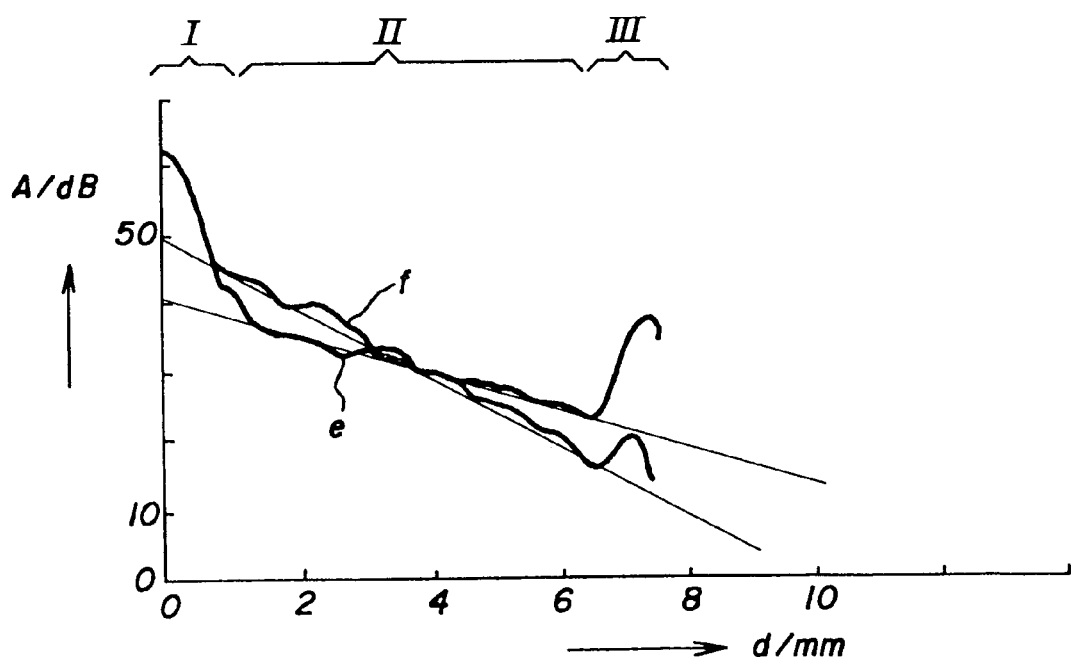
FIG. 2 is a diagram in which the amplitude of the ultrasonic echo signal received by the ultrasonic receiver for a porous component and a nonporous component with a thickness of approximately 8 mm is plotted against the depth (transit time)

In the diagram according to FIG. 2, in curves e and f the measured amplitudes A of the received ultrasonic signal are respectively plotted against the depth d (transit time) for two components with a thickness of 7 mm. Curve e reproduces the amplitudes measured on a component with low porosity and curve f reproduces the amplitudes measured on a component with high porosity. Both curves are made up of three regions I, II, III. In the region I that is near the surface, the signal variation is substantially characterized by the entry echo signal. On account of the pronounced entry echo, the region I forms a zone which cannot be used for the evaluation and, given a test frequency of 5 MHz, is in practice approximately 1–2 mm. This is followed by the region II, in which, given constant porosity, the amplitude A of the received ultrasonic echo signal decreases on average approximately linearly with increasing depth d (approximately constant average slope), until finally a renewed amplitude increase is measured in the region III, which is to be assigned to the back-wall echo signal. In this graph it can consequently be clearly seen that the amplitude A of the received ultrasonic signal in the case of the porous component decreases significantly more clearly with increasing depth d (greater amount of average slope) than in the case of a component with low porosity.

Figure 3:
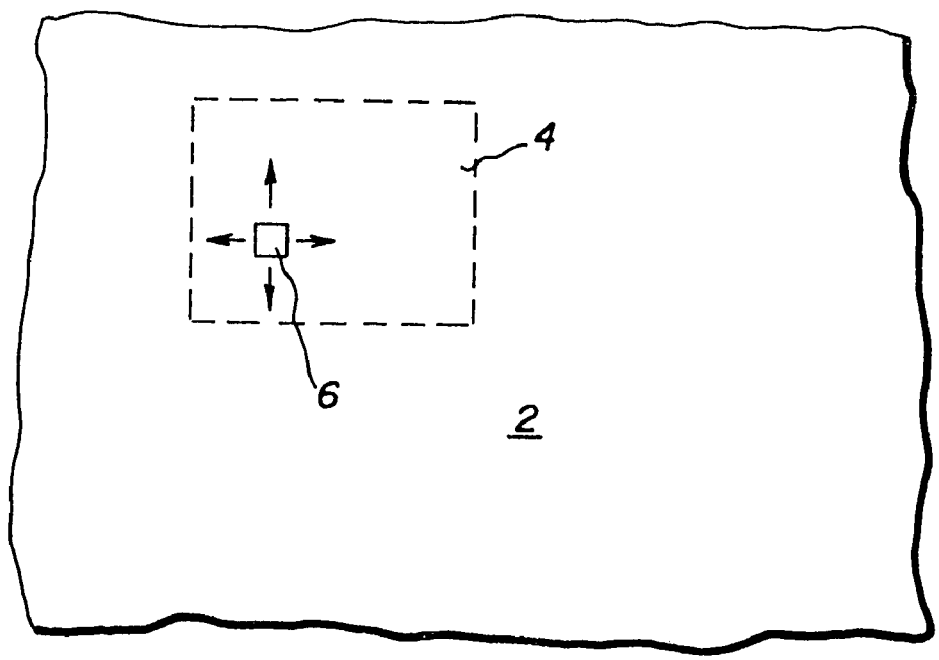
FIG. 3 is a plan view onto a component to be tested, with a schematically illustrated test head.
Figure 4:
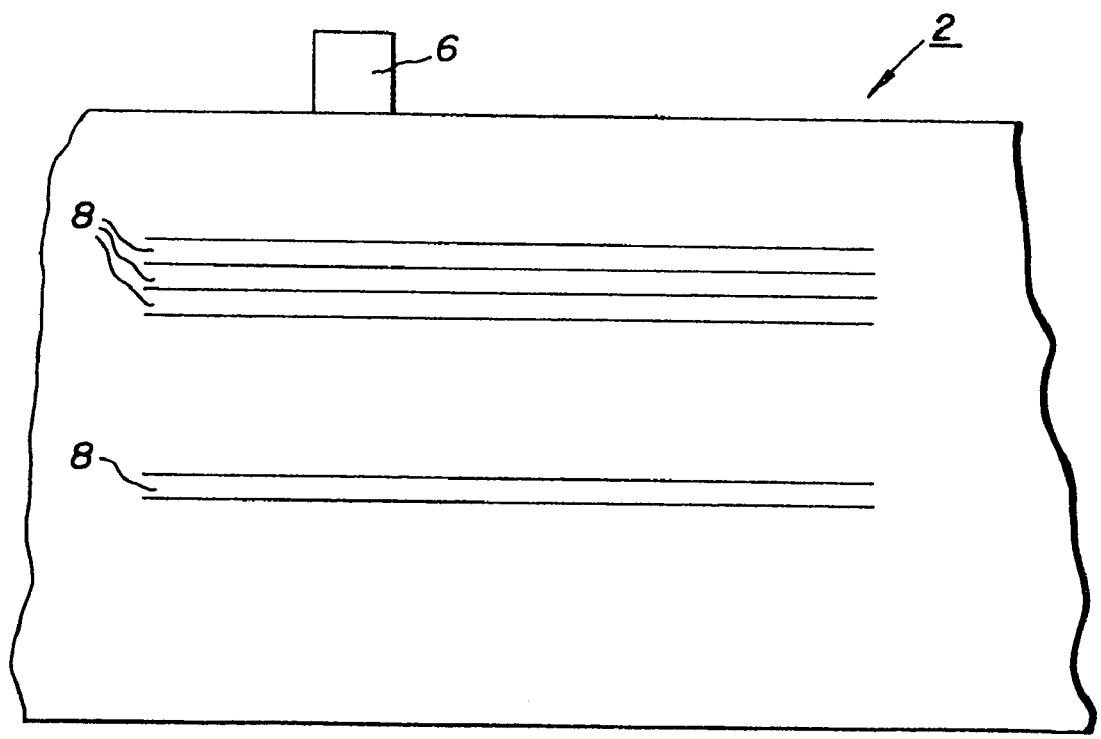
FIG. 4 is a section through the component to be tested.

The procedure according to the invention is explained in more detail on the basis of FIGS. 3 and 4. FIG. 3 shows a schematic plan view of a component 2, from which an area region 4 to be assessed—in the exemplary embodiment represented by a rectangular surface region—is selected and in which a number of measurements are carried out in different test positions with the aid of a test head 6. For this purpose, as illustrated by arrows, the test head 6 is positioned in different test positions of the surface region 4 and a measurement is performed in each of these test positions. In the exemplary embodiment represented, a test head 6 is provided with an ultrasonic transducer, which serves as a transmitter and receiver. In principle, transmitting and receiving transducers may also be arranged separately from each other. This has the advantage that the amplitude in the region I (entry echo) is reduced, and consequently the measuring range nearer to the surface of the component is expanded.

A rotationally symmetrical transducer configuration, for example a circular-disk-shaped transmitting transducer which is surrounded by a circular-ring-shaped receiving transducer, is advantageous in particular. It is ensured by the rotational symmetry that the measurement results are independent of the rotational orientation of the test head.

In the component 2 according to FIG. 4, a multiplicity of layers 8 of different depths d arranged parallel to the surface are defined and respectively assigned on the basis of the transit time an amplitude A of the ultrasonic signal received by the ultrasonic receiver 6. In this case, the layer thickness of these layers 8 does not have to coincide with the thickness of the individual layers of the composite material.

The ultrasonic amplitudes measured in different test positions and for different layers 8 are then statistically evaluated, for example by forming the arithmetic mean value of the amplitudes that belong to a layer and are respectively determined in the various test positions. Such a statistical evaluation in a number of test positions is required, since in one test position there does not necessarily have to be a relevant amplitude of the ultrasonic echo signal for each layer 8.

Figure 5:
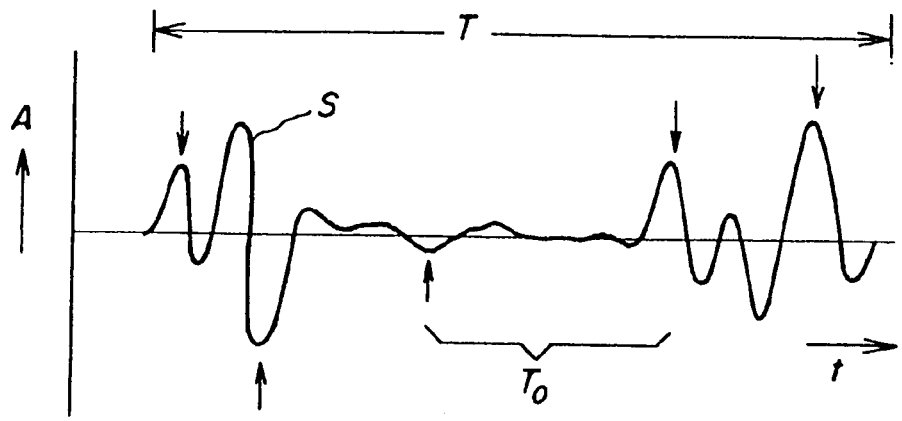
FIG. 5 is a graph showing the signal variation over time of the ultrasonic signals received by the ultrasonic receiver.

A particularly suitable method of detecting the relevant amplitudes of the ultrasonic echo signal is a so-called ALOK method, in which the receiving device operates with a time aperture (time window T) that is longer than the thickness of the respective layer to be detected. The acronym ALOK represents the German "Amplituden Laufzeit Ortskurven", which translates to Amplitude Time Locus Curves. Additional information may be found at http://www.ndt.net (The e-Journal of Nondestructive Testing) and, more specifically, at http://www.ndt.net/article/dresd97/csapo/csapo_e.htm and at http://www.ndt.net/article/az/ut_idx.htm. In the ALOK method, a relevant amplitude is detected on the basis of the signal variation of the received ultrasonic echo signal by the amplitude of the ultrasonic echo signal between at least one ultrasonic half-wave before this amplitude and an ultrasonic half-wave after this amplitude being of an amount greater than the amplitude of these half-waves. This is explained in more detail in FIG. 5 on the basis of a variation given by way of example of an ultrasonic echo signal S detected within the chosen time window. With this method, amplitudes that are detected as relevant are highlighted by an arrow. On the basis of the transit time t (depth), each relevant amplitude is assigned a layer. It can be seen in the figure that relatively great time ranges $T_0$ in which a relevant amplitude is not measured may also occur, so that, in the case where this time window is greater than the layer thickness, there is no relevant amplitude for this layer.

Figure 6:
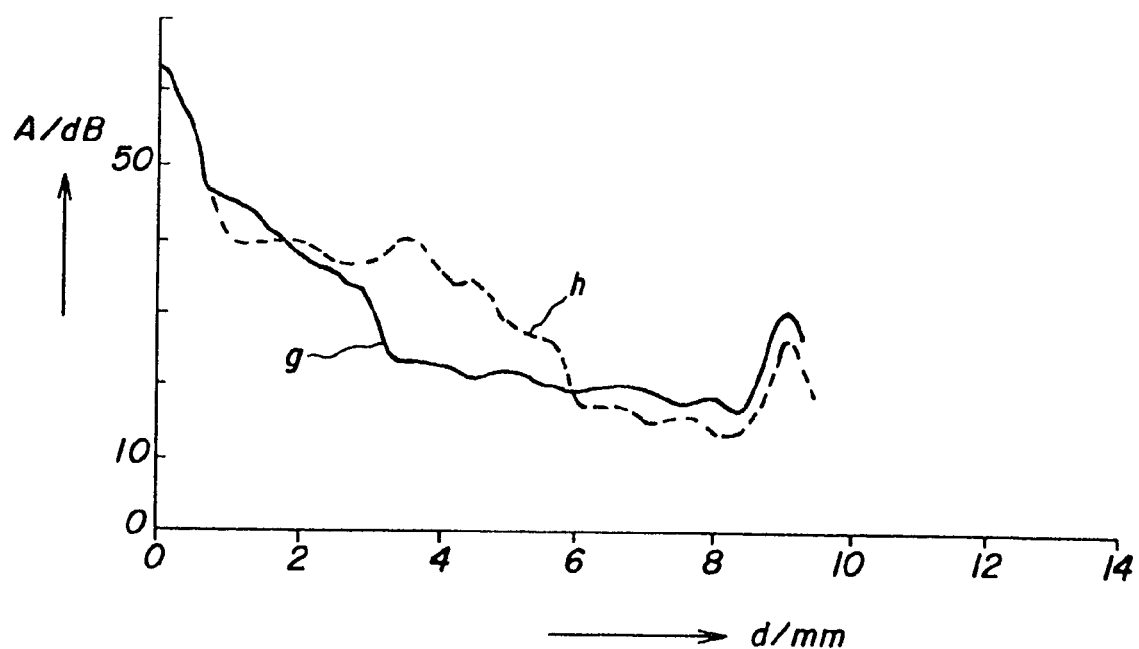
FIG. 6 is a diagram in which the amplitude of the received ultrasonic signal for a component with a thickness of approximately 9 mm is plotted against the depth for two different components.

In the diagram according to FIG. 6, measurements on two porous CFR components are reproduced in curves g, h. The amplitude A of the ultrasonic echo signal is plotted against the depth d (transit time). It can then be seen from the different slope of the individual curves g and h that, in the case of the component reproduced by the curve g, the porosity in the proximity of the surface is greater on account of the greater steepness than the porosity in the middle of the component or in the proximity of the back wall. In curve h it can then be seen that a rise in the amplitude of the backscattered echo signal takes place in the middle of the component, with subsequently a slope of a greater amount (steeper drop) than in the region near the surface. This suggests increased porosity in the middle of the component. It can then be concluded from the virtually equal amplitude of the back-wall echo for both components that the porosity value averaged over the depth d of the two components is approximately the same.

This application claims the priority, under 35 U.S.C. §119, of German patent application No. 103 29 142.3, filed Jun. 27, 2003; the entire disclosure of the prior application is herewith incorporated by reference.

I claim:

1. A method of determining the porosity of a workpiece, which comprises:
   injecting an ultrasonic signal into the workpiece;
   receiving an ultrasonic echo signal generated in a depth within the workpiece; and
   determining a variation of an amplitude of the ultrasonic echo signal with respect to said depth, and using the variation of the amplitude as a measure of the porosity at the respective depth.

2. The method according to claim 1, which comprises injecting the ultrasonic signal into a workpiece made of a fiber composite material.

3. The method according to claim 1, which comprises:
   dividing the workpiece in an area region to be investigated into a plurality of layers of mutually different depths;
   placing an ultrasonic test head onto the area region in a test position, injecting the ultrasonic signal into the workpiece with the test head, receiving the ultrasonic echo signal from the workpiece, and measuring the amplitude belonging to each layer; and
   using a variation of the amplitude with respect to the depth of the layer as a measure of the porosity in the respective layer.

4. The method according to claim 3, wherein the area region is defined with a number of test positions and the method further comprises averaging the amplitude of the ultrasonic echo signal belonging to the individual layers respectively measured in the individual test positions.

5. The method according to claim 3, which comprises analyzing the received ultrasonic echo signal and determining the amplitudes of the ultrasonic echo signals belonging to a layer by identifying amplitudes within a time window belonging to said layer being of an amount greater than the amplitudes of the echo signal a half-wave before and a half-wave after the amplitudes.

6. The method according to claim 1, which comprises using an average slope of the ultrasonic echo signal, in dependence on a depth d, as the measure of the porosity.

* * * * *